United States Patent [19]

Shah

[11] Patent Number: 4,583,917

[45] Date of Patent: Apr. 22, 1986

[54] PRESSURE REGULATING AND MONITORING DEVICE

[76] Inventor: Nayan S. Shah, 6821 Sutherland Ct., Mentor, Ohio 44060

[21] Appl. No.: 718,196

[22] Filed: Apr. 1, 1985

Related U.S. Application Data

[63] Continuation-in-part of Ser. No. 505,462, Jun. 17, 1983, abandoned.

[51] Int. Cl.$^4$ ............................................. F04B 21/00
[52] U.S. Cl. .................... 417/63; 128/207.15; 417/374; 417/437; 417/440; 604/97; 604/99; 604/100
[58] Field of Search ............... 128/207.15, 207.16; 604/97, 98, 95, 99, 100, 101; 417/63, 234, 374, 510, 437, 435, 440, 312; 73/1 H, 4 R, 302; 137/882, 589, 583, 587, 599.2; 251/118

[56] References Cited

U.S. PATENT DOCUMENTS

| | | | |
|---|---|---|---|
| 1,649,530 | 11/1927 | Holsinger | 417/63 X |
| 2,785,852 | 3/1957 | Bramming | 417/437 |
| 3,046,966 | 7/1962 | Butler et al. | 417/63 X |
| 4,063,824 | 12/1977 | Baker et al. | 417/312 X |
| 4,133,349 | 1/1979 | Stripling | 137/882 |
| 4,147,180 | 4/1979 | Steele | 137/599.2 |
| 4,182,344 | 1/1980 | Benson | 138/31 X |
| 4,245,639 | 1/1981 | La Rosa | 604/97 |
| 4,280,909 | 7/1981 | Deutsch | 417/572 X |
| 4,297,081 | 10/1981 | Irvin | 417/63 X |
| 4,305,701 | 12/1981 | Geil | 417/437 X |
| 4,351,330 | 9/1982 | Scarberry | 128/207.15 |
| 4,370,982 | 2/1983 | Reilly | 604/98 |
| 4,409,833 | 10/1983 | Thomson et al. | 73/302 |

Primary Examiner—Edward K. Look
Attorney, Agent, or Firm—Hill, Van Santen, Steadman & Simpson

[57] ABSTRACT

A hand held device for regulating and monitoring air pressure. The device comprises an elongate barrel having a crown end and an opposite end attachment structure for connecting the device to a point of use such as an inflatable endotracheal cuff. A plunger pump in the barrel is digitally operable at the crown end for generating air pressure within a chamber the in barrel. A pressure monitoring gauge is carried by the barrel. Air pressure generated by the plunger pump communicates from the chamber through the attachment structure with the point of use, and through a mercury reservoir with the pressure monitoring gauge. A second digitally operable plunger carried by the barrel and engageable at the crown end is adapted for selectively releasing the air pressure from the chamber.

35 Claims, 8 Drawing Figures

PRESSURE REGULATING AND MONITORING DEVICE

This is a continuation, of application Ser. No. 505,462, filed June 17, 1983, now abandoned.

BACKGROUND OF THE INVENTION

1. Field of the Invention

This invention relates to a new and improved hand held pressure regulating and monitoring device, and is more particularly concerned with a device especially useful for regulating and monitoring pressure within a chamber such as an inflatable cuff forming a part of a medical apparatus, although it will be apparent that the device has wider utility.

Merely by way of example, it may be mentioned that during certain types of surgical procedures, anesthetic is administered to a patient by using an endotracheal tube having an inflatable cuff which is inflated by source of pressurized air. When the cuff is properly inflated, the endotracheal tube is restrained against slippage by the pressure of the cuff against the mucosal wall of the trachea.

Even though the cuff is made from materials impervious to air, certain types of anesthetics are capable of passing through the walls of the cuff, thereby increasing the gas pressure therein. Often this increase in gas pressure exerted by the over-inflated cuff of the endotracheal tube can result in damage to the mucosal wall of the trachea, which in some instances may be irreversible. Consequently, it is extremely important that the cuff pressure be maintained at an as nearly as practicable optimum value, e.g. approximately 25 mmHg.

2. Prior Art

In order to monitor the cuff pressure, mechanical or mercury manometers have heretofore been used. Those devices are frequently cumbersome due to their size and they occupy valuable space within an operating room, recovery room or even in a patient's room. They also can be a serious distraction during critical operating procedures. Such manometers also contain a large amount of dead air space in the connecting tubes, and hence pressure readings are frequently inaccurate.

A significant improvement is disclosed in the pending application of John Pistillo Ser. No. 461,267 filed Jan. 26, 1983 and assigned to the present applicant. The device and method disclosed in that application are adapted to be applied to the tube by which the inflatable cuff is inflated, after the tube has been disconnected from an air or other gas source under pressure. The device of the prior application provides a hand held pressure monitoring device and which has the capability of modifying the air pressure in the cuff within a rather limited range, and is not adapted to provide the initial or basic cuff inflating air pressure.

SUMMARY OF THE PRESENT INVENTION

It is to the improvement of devices as represented in the aforesaid pending application that the present invention is particularly directed, and especially to provide the capability in a small size hand held device for not only digitally generating the desired air pressure for the point of use such as an inflatable cuff or the like, but also for digitally releasing the air pressure for adjusting to a preferred pressure from a possibly overinflated condition or for entirely deflating when desired. This permits a doctor or technician to closely regulate and monitor pressure by means of the small hand held device without significant distraction during the particular medical or other procedure in connection with which the device is employed.

A further aim is to provide a device for the described purpose which is adapted to be of such a small and convenient size that it can be readily carried by the doctor or technician in a garment pocket for quick accessibility.

In one aspect the invention provides a new and improved hand held pressure regulating and monitoring device, comprising an elongate barrel having a crown end and an opposite end including means for attachment of the device to a point of gas pressure use, first means carried by the barrel for providing gas pressure in the barrel, pressure monitoring means carried by the barrel, means for effecting communication of the gas pressure with the monitoring means and with the point of use, and second means carried by the barrel and digitally operable at the crown end for selectively releasing the gas pressure.

BRIEF DESCRIPTION OF THE DRAWINGS

Other objects, features and advantages of the present invention will be readily apparent from the following description of certain representative embodiments thereof, taken in conjunction with the accompanying drawings, although variations and modifications may be effected without departing from the spirit and scope of the novel concepts embodied in the disclosure, and in which.

DETAILED DESCRIPTION

Figures 1, 2, 4, 5:
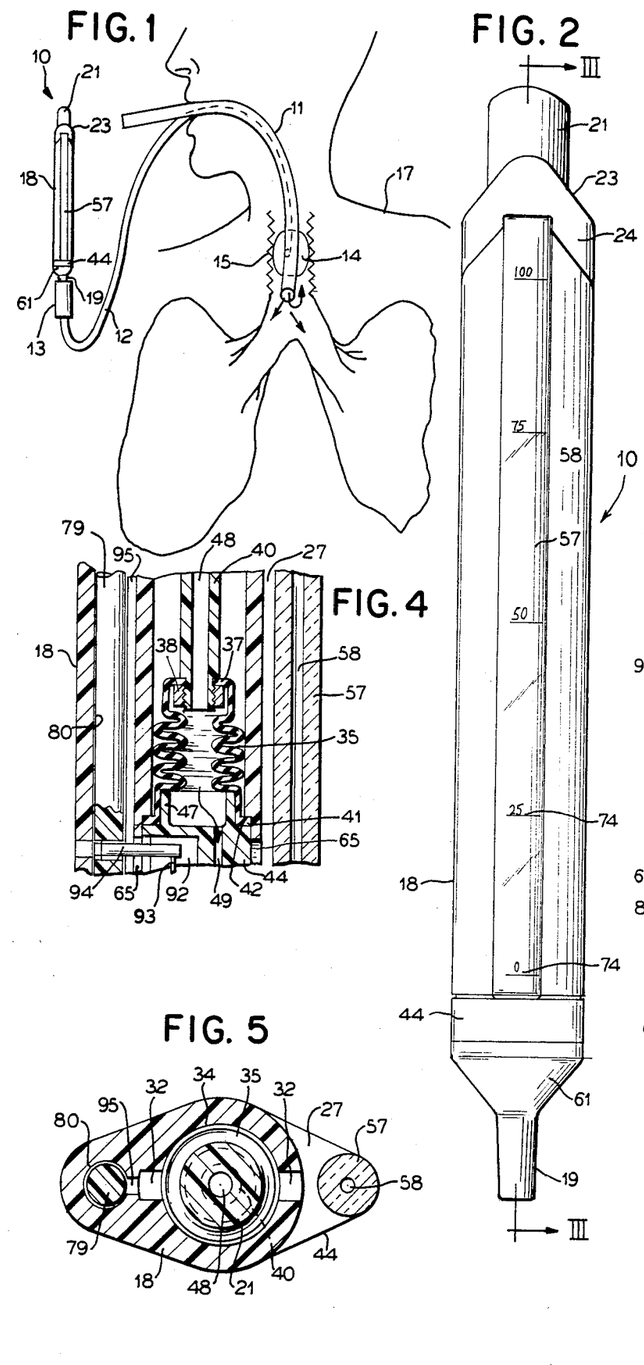
FIG. 1 is an elevational view, partially in phantom of an endotracheal tube in conjunction with a pressure regulating and monitoring device of the present invention.
FIG. 2 is an enlarged front elevational view of the device.
FIG. 4 is a fragmentary similar sectional detail view showing the pumpng device in an end of pumping stroke position.
FIG. 5 is a horizontal sectional detail view taken substantially along the line V—V of FIG. 3.

As exemplified in FIG. 1, a hand held pressure regulating and monitoring device 10 constructed according to, and adapted to practice the method of, the present invention is adapted to be connected with a point of gas pressure use, e.g. a medical apparatus such as an endotracheal tube 11, by means of a flexible tube or duct 12 which has an outer end coupling 13 to which the device 10 is adapted to be releasably connected. Since the duct 12 is of much smaller diameter then the inside diameter of the tube 11, the duct 12 is adapted to pass freely through the tube 11 to terminate in the area of an inflatable bulb or cuff 14 providing a sealed enclosure surrounding the tube 11 which is of substantially smaller diameter then the inside of a trachea 15.

In use, the endotracheal tube 11 is inserted through the mouth of a patient 17 and is advanced into the trachea 15 where the inflatable cuff 14 is inflated by means of air introduced through the air duct 12. Air under pressure may be derived from a conventional air source, but is preferably generated by means of the device 10 as will be described hereinafter. The inflatable cuff 14 is inflated to a predetermined pressure to retain the tube 11 within the trachea 15. However, it is important to maintain the pressure within the cuff 14 as nearly as practicable at about 25 mmHg in order to avoid damage to the mucosal wall of the trachea. For various reasons the pressure in the cuff 14 may increase due to expansion of the air in the cuff without additional air input. For example, due to the material from which the cuff 14 is made anesthetic delivered to the lungs of the patient through the duct 11 may pass through the wall of the cuff and thus increase the intracuff pressure.

According to the present invention, the device 10 provides a convenient small hand held instrument adapted for not only providing cuff-inflating air pressure, but also for enabling monitoring the air pressure, and for releasing air pressure if necessary to maintain a predetermined cuff pressure. To this end, the device 10 comprises an elongate barrel 18 which may be of generally fountain pen size so that it can be easily carried in a hospital uniform pocket of an anesthesiologist or other technician for one handed manipulation and use as needed.

At one end the barrel 18 has means for effecting connection with the air tube connector 13 which may, for example, comprise a luer adaptor. A tapered nipple 19 is suitable for this purpose so that the device 10 can by means of the nipple be readily slipped into assembly with the connector 13 or pulled off as necessary. As is customary, the luer adaptor 13 has a one way self-closing resilient valve. Means extending longitudinally through the nipple 19 for effecting communication of air pressure within the barrel 18 with the point of use comprises an air passage 20 through which air is adapted to be pumped from within the barrel 18 by means carried by and within the barrel 18 and comprising a digitally manipulatable plunger 21 which has a head end terminal portion normally projecting upwardly through a crown 22 on the end of the plunger opposite to the nipple 19. In a preferred construction the crown 22 is a surface upon an outer end surface of a hollow cap member 23 which is complementary to and secured on the contiguous end of the barrel 18. A skirt flange 24 on the cap member 23 seats on the end of the barrel 18 and defines with the barrel end a cavity 25 which opens to atmosphere in a space 27 (FIGS. 3 and 5) at what may be referred to as the front side of the barrel.

Figure 3:
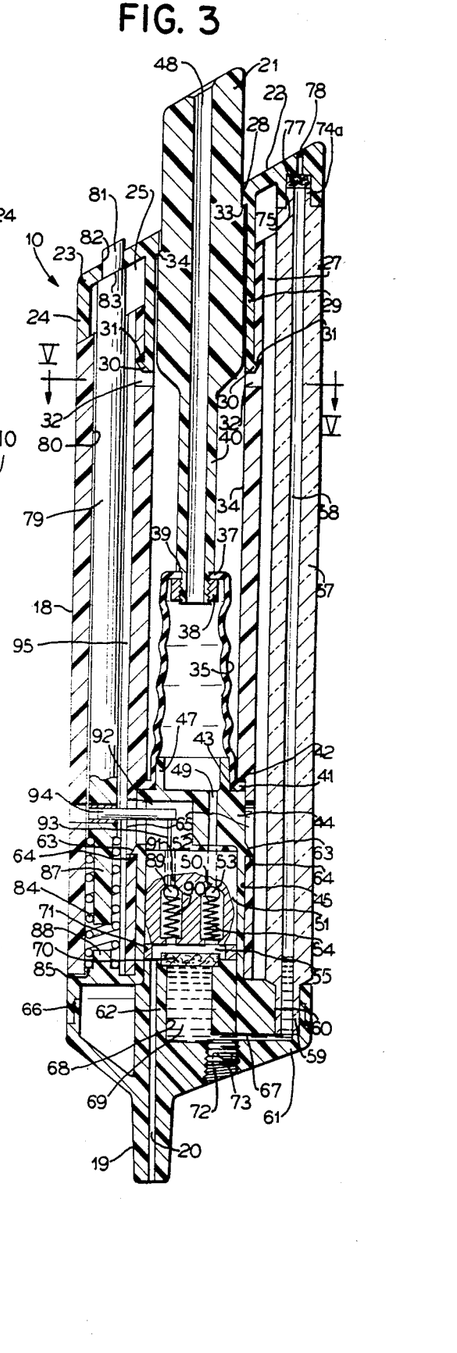
FIG. 3 is a vertical sectional detail view taken substantially along the line III—III of FIG. 2 and showing the digitally operable pump of the device in a protracted or start of pumping stroke position.

For reciprocably guiding the preferably elongate cylindrically shaped plunger 21, the cap member 23 has a plunger guide hole 28 opening through the crown 22 and aligned with an inwardly extending integral tubular plunger guide and cap retaining projection 29. At its inner end the projection 29 has diametrically oppositely extending interlock prongs 30 which are adapted for resiliently snapping into retaining engagement with interlock shoulders 31 provided at diametrically opposite, combined shoulder defining and air relief ports 32 formed in the wall of the barrel 18. At the inner end of the hole 28 is an inwardly facing annular shoulder 33 which is engageable as a stop by an annular axially outwardly facing stop shoulder 34 on the perimeter of the plunger 21.

In length, the plunger 21 is somewhat shorter than the combined lengths of the bore 28, the entire length of the tubular inward projection 29 and the length of a plunger guiding bore 34 extending within the barrel 18 inwardly from the projection 29. This provides for a substantial range of axial movement of the plunger 21 within the barrel between an outwardly protracted limit position defined by the shoulders 33 and 34, and an inwardly depressed end of pumping stroke position of the plunger. Automatic return of the plunger 21 from a pumping stroke is effected by a resiliently compressible corrugated substantially frustoconical tubular pumping bellows 35 attached at its smaller diameter end to the inner end of the plunger. A radially inwardly extending annular flange 37 on the head end of the bellows 35 is secured as by means of a ring nut 38 to an annular shoulder on an inner end reduced diameter portion 40 of the plunger 21. At its opposite large diameter foot end, the bellows 35 has a radially outwardly extending annular flange 41 which is clamped between opposed complementary clamping shoulders 42 and 43 on respectively the barrel 18 and an axial fitting insert 44 extending upwardly within a downwardly opening extension 45 of the barrel bore 34. Within the larger diameter end of the bellows 35 is an annular axially extending stabilizing flange 47 on the inner end of the insert 44.

When the plunger 21 is depressed inwardly by a digit such as a thumb of the hand in which the barrel 18 is held, the outer end of an axial air passage 48 in the plunger 21 is closed and air trapped in such passage and within the bellows 35 into which the passage 48 opens is compressed and displaced through an axially extending displacement port in the insert 44 and into an aligned axially extending air pressure transfer passage 50 in a valve block 51 mounted within a complementary cavity in the insert 44. A sealing means such as a ring 52 seals the joint about the communicating ends of the port 49 and the passage 50. In the passage 50 a one way check valve 53 biased as by means of a coiled compression spring 54 permits pumped air pressure to be driven by pump pressure past the check valve 53 into a chamber 55 at the discharge end of the check valved passage 50. At its inner end, the passage 20 leading through the nipple 19 communicates with the chamber 55 for conveying the pressurized air to the point of use.

In order to monitor the air pressure as it is generated by operating the pump plunger 21, means are provided comprising a pressure gauge carried by the barrel 18 and including a transparent sighting tube 57 conveniently mounted parallel to the barrel axis and on the front side of the barrel having regard to the manner in which the device 10 is grasped for use. In a desirable construction, the pressure gauge tube 57 has a longitudinal channel or bore 58 which opens through the opposite ends of the tube 57. One end of the bore 58 opens through what may be regarded as the lower or foot end of the gauge tube 57 considered from the viewpoint of FIG. 3. For convenience in assembly, a reduced diameter foot end terminal portion 59 of the tube 57 is received in a complementary socket 60 provided in part by a fitting 61 which carries integrally therewith the connecting nipple 19 and has a central inwardly opening boss 62 interfitting in assembly with a lower extension portion of the fitting member 44 which houses the valve block 51.

For snap-together assembly with the barrel 18, the member 44 has diametrically opposite radially outwardly project interlock prongs 63 which interlock with respective shoulders 64 provided therefore by longitudinally extending slots 65 in the lower portion of the body of the barrel 18. When assembling the device, the fitting 61 and the member 44 are adapted to be fastened together by means of a telescopic joint 66 and the subassembly thus constructed is assembled with the lower end portion (as viewed in FIG. 3) of the barrel 18 by slipping the upper portion of the member 44 in to the barrel bore portion 45 until final assembly is attained. The plunger 21 and the attached bellows 35 are preassembled in the barrel 18 and as the final asembled relation of the fitting subassembly 44, 61 is attained, the bellows flange 41 is clamped in place.

At its foot end, the pressure gauge tube bore 58 communicates by means of a radially extending passage 67, provided by and between the members 44 and 61, with the lower end of an upwardly opening reservoir 68 in the fitting member boss 62. Mercury 69 fills the reservoir 68, the passage 67 and the lower end portion of the pressure gauge bore 58 and is adapted to be displaced upwardly in the bore 58 by air pressure in the pressure chamber 55 above the upper end of the reservoir 68. Means impervious to mercury, but air pervious, comprising a microporous membrane or screen 70 is mounted fixedly across the top of the reservoir 68 and spaced below the valve block 51, a packing and spacer ring 71 maintaining the space for the pressure chamber 55 between the top of the boss 62 and the bearing block 51.

Means for filling the mercury 69 into the reservoir 68 and for attaining initial mercury height adjustment in the gauge bore 58 comprises a filler opening 72 in the fitting 61, and a closure plug and mercury height adjustment plug 73 threadedly secured in the opening 72. In a sense, also, the filler opening 72 serves as a supplementary reservoir. When filling the mercury spaces with the mercury, before the plug 73 is secured in place, a precalculated volume of the mercury 69 is loaded into the mercury spaces, and then the plug 73 threaded into the opening 72. Enough mercury is loaded into the mercury spaces so that by threadedly adjusting the plug 73, an initial gauge setting height of the mercury column in the gauge bore 58 can be accurately attained. For example, where the pressure gauge tube 57 is calibrated by indicia 74 (FIG. 2) from 0 mmHg upwardly, such as by 25 mm increments, the initial, non-operating or starting height of the mercury column in the gauge bore 58 may be adjusted to be at the 0 indicia mark. Then as pressure develops in the chamber 55, the mercury column will be caused by the air pressure to rise in the gauge bore 58. Thereby observation of the pressure gauge will reveal the pressure attained. As long as the device 10 is connected with the air duct 12, the pressure gauge will indicate the pressure at the point of use such as in the expansible cuff 14.

At its head or upper end, the gauge tube 57 is secured in place by reception of a terminal portion 74 engaged in a downwardly opening socket 75 provided by an overhanging front portion of the cap 23. Although the upper end of the gauge bore 58 may be sealed so that air trapped above the mercury column is compressed and thus serves to provide a mercury column return biasing means when the mercury column is caused to rise in the bore, the upper end of the gauge bore 58 is desirably left open to ambient atmospheric pressure. Air pervious, but mercury impervious, filter means comprising a plug 77 secured across the end of the bore 58 between the terminal 74 and an air relief port 78 in the cap 23 permits free passage of air but prevents mercury leakage should some of the mercury migrate to this end of the bore 58, as, for instance, if the device 10 is upended.

To assist in maintaining a preferred pressure as monitored by means of the pressure gauge system of the device 10, digitally operable means are provided for modulating the air pressure generated by means of the air pressure pump of the device. For this purpose the barrel 10 carries a depressable axially upwardly projecting pressure relief plunger 79 reciprocably mounted in a bore 80 in a rear portion of the barrel 18 in spaced parallel relation to the pumping plunger bore 34. A digitally operable upwardly projecting button-like terminal 81 on the plunger 79 projects through a clearance bore 82 in the cap 23. An axially outwardly facing shoulder 83 on the plunger 79 about the base of the terminal 82 is engageable as a limit stop against the inside of the cap 23 about the clearance bore 82. Normally the plunger 79 is biased upwardly as by means of a coiled compression spring 84 thrusting against the lower end of the plunger 79 and seated against a thrust shoulder 85 provided by the portion of the fitting member 44 which underlies and closes the lower end of the bore 80. A depression limit stop for the plunger 79 in opposition to the spring 84 is provided by a reduced diameter lower end terminal 87 on the plunger which opposes an upwardly projecting reduced diameter stop extension 88 on the boss 85 within the lower end of the biasing spring. The space between the stop projections 87 and 88 in the outwardly biased condition of the plunger 79 is sufficiently less than the length of the digitally engageable head terminal 81 to permit a short outer end portion of the terminal 81 to remain projecting above the crown surface 22 in the fully depressed position of the plunger 79.

For releasing pressure from the chamber 55, a check valve 89 within the valve block 51 and normally biased into closed position by means of a biasing spring 90 is adapted to be operated by means of the plunger 79. Conveniently, the check valve 89 is of the same type as the check valve 53, being mounted in a passage 91 which opens to the chamber 55 at its lower end and at its upper end opens into a chamber 92 provided in the fitting member 44 above the valve block 51 and with the adjacent clearance slot 65 communicating therewith and with the adjacent portion of the plunger bore 80. Opening of the check valve 89 is adapted to be effected by means of a downwardly projecting depressor finger 93 carried by a radially extending arm 94 projecting from the plunger 79 through the adjacent clearance slot 65 and into the chamber 92. Through this arrangement, the check valve 89 is normally closed whereby to maintain generated air pressure in the pressure chamber 55. When the plunger 79 is depressed, the finger 93 opens the valve 89 to permit escape of air pressure through the passage 91 into the chamber 92 and then out through the adjacent slot 65 to the plunger bore 80. To facilitate air escape, the bore 80 is provided with a parallel air escape channel 95. which communicates with the adjacent slot 65 acting as an air escape port at the lower end of the channel 95. The upper end of the channel 95 opens into the air space 25 in the cap 23 and which opens to atmosphere in the vertical air space 27 between the barrel 18 and the pressure gauge tube 57. (FIGS. 3 and 5).

To facilitate one handed carrying and operation of the device 10, both for air pressure generation by means of the pump plunger 21, and to control or modulate the air pressure by means of the air release plunger 79, the crown 22 is constructed on a front to rear bias or slope, and the head end terminal of the plunger 21 normally extends to a substantially greater height above the crown 22, both in the projected position of the plunger 21 and in its fully depressed position, than the maximum upward projection of the pressure release plunger terminal 81. Thereby the pump plunger 21 can be freely digitally manipulated, as for example, by the thumb of the hand holding the device 10, without interfering with the pressure release plunger terminal 81. In other words a full range of operation of the plunger 21 is provided for without contact of the pumping digit with the pressure release plunger terminal 81. However, simply by shifting the operating digit from the top of the plunger 21, to the top of the terminal 81, operation of the pressure release means is effected. This permits the user of the device 10 to perform all of the digital manipulations for generating pressure and for releasably modulating the pressure one handedly, while the other hand is left free for any other desired manuever.

In operation, after the device 10 has been installed on the pressure duct 12, the pump plunger 21 is digitally manipulated by pressing down on its crown terminal whereby the air passage 48 is closed and the air trapped in the pump assembly is displaced in pressurizing direction as indicated by arrow in FIG. 4. As the pump bellows 35 is collapsed, it developes a spring biasing load which when the plunger 21 is released and the passage 48 opened to atmosphere, automatically returns the plunger 21 to protracted position and refills the pump with air. This pumping action can then be repeated until the desired air pressure has been generated at the point of use, e.g. the inflatable cuff 14. As the air pressure is generated, it can be monitored by observation of the pressure gauge 57. If an overpressurized condition is observed, pressure can be quickly relieved by depressing the pressure release plunger 79. Then, in the course of the function for which the pressurized air is supplied, pressure can be selectively increased or reduced by alternate operation of the pump plunger 21 and the pressure release plunger 79 so that a desired median pressure can be constantly maintained. When pressurized air need terminates, the system can be purged of pressurized air by holding down the pressure release plunger 79 until the system is purged. The device 18 may be readily detached from the use system such as by detaching it from the connector 13, and transported to another point of use or stored, as for example in a user's pocket.

Although the device 10 has been illustrated by way of example for use in regulating and monitoring pressure in an endotracheal tube and inflatable cuff arrangement, it will be appreciated that the device may be utilized with other types of pressure utilizing instruments. For example, the device 10 may be utilized with tracheostomy tubes or catheters utilizing inflatable cuffs or other types of gas filled envelope or enclosure arrangements.

The device 10 may be made of any suitable materials, such as impact resistant plastic or glass. In particular, the barrel 18 and various components assembled therewith may be molded from plastic, including the plungers 21 and 79. The pressure gauge tube 57 may be made from glass or clear plastic. The various springs may be any suitable material but because of their small size may generally be made from suitable spring metal. The bellows 35 may be made from a suitable elastomer.

Figure 6:
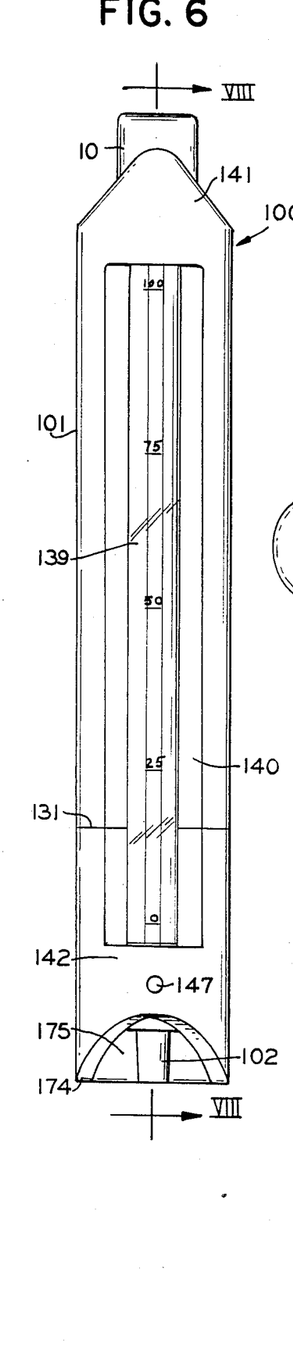
FIG. 6 is a front elevational view of a modification of the monitoring device of the present invention.
Figures 7, 8:
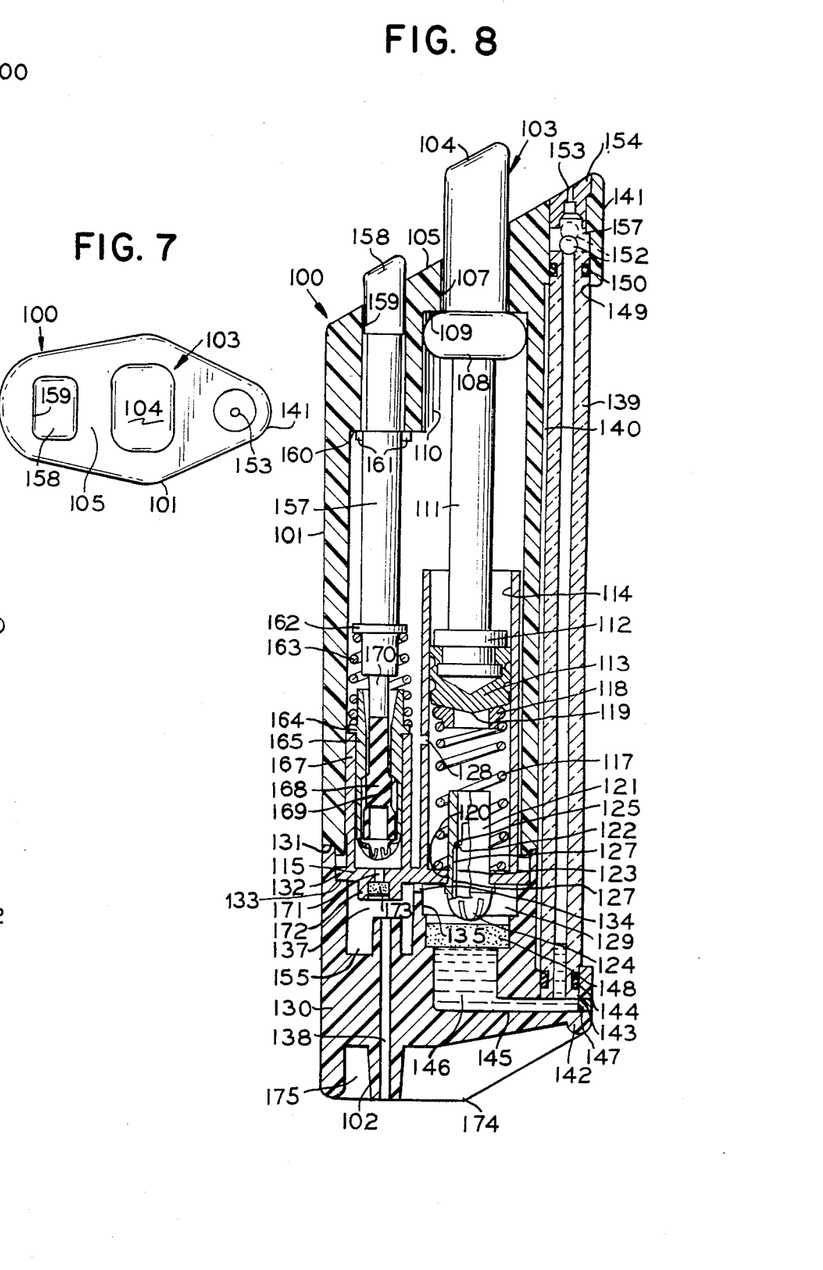
FIG. 7 is a top plane view of the device of FIG. 6.
FIG. 8 is a vertical sectional detail view taken substantially along the line VIII—VIII in FIG. 6.

A modified form 100 of the device is disclosed in FIGS. 6-8. This device 100 is also of the generally fountain pen size so that it can easily be carried and manipulated by a technician for one-handed manipulation, and comprises an elongate barrel 101, having at its lower end a tapered nipple 102 adapted for assembly with the connector 13 in FIG. 1, similarly as described for the nipple 19 in FIG. 2.

Within the barrel 101, is longitudinally reciprocatingly mounted a digitally manipulatable air pressurizing pump plunger 103, which has an upper end elongated head terminal 104, normally projecting above a crown surface 105 which desirably slants rearwardly. For retaining the plunger terminal 104 against turning relative to the crown 105, with respect to which the top of the terminal 104 is complementally slanted, the terminal is desireably of non-circular cross-section, such as of the generally rectangular form shown and is loosely slidibly guided in a guide bore 107 of complementary shape. Limit on outward projection of the plunger terminal 104 is effected by means of a reciprocation stabilizing and stop-collar 108, which is engagable with an inwardly facing stop shoulder 109 about the inner end of the guide bore 107. The collar 108 is freely reciprocably guided within what may be a coaxial cylindrical inward guideway extension 110 from the bore 107. About its perimeter, the collar 108 is preferably of arcuate cross-section for not only limiting contact with the wall defining the cylindrical bore guideway 110, but also to minimize resistance to relief air movement past the collar during reciprocations of the plunger.

An elongate stem 111, projecting inwardly on the plunger coaxially from the collar 108, carries at its inner end an annularly grooved piston 122, with which is interlocked a perferably elastomric, annularly grooved piston head 113, engaging in substantially air tight sliding contact within a coaxial upwardly opening tubular cylinder 114 fixed within the barrel 101. An upwardly facing seat 115, in the bottom of the cylinder 114, has a coiled compression spring 117 thrusting thereagainst and of a length to thrust upwardly toward and against the piston 112, which in the extended position of the plunger 103 is substantially spaced above the seat 115.

Upward thrust of the spring 117 is imparted to the piston 113 by means of a centering ring 118 mounted on the upper end of the spring, and engaging the lower end of the piston which has a centering frustoconical tip 119 for this purpose.

Fixed to the bottom of the cylinder 114, within a concentric hole 120 in the seat or base 115, is a spring-type check valve 121, of a well-known type having a generally cylindrical tubular casing within which is mounted an elastomeric valve member 122, having a thin tubular spring lower end portion 123 thrusting downwardly against a seat and air passage configuration 124. The valve normally closes against a seat 125 within the valve body, and is adapted to be blown downwardly from the seat in opposition to the bias of the valve spring 123 by air pressure generated by the piston 113 in the cylinder 114. Longitudinal grooves 127 in the perimeter of the valve 122 permit air to escape downwardly past the valve and through the air passages in the base configuration 124 of the valve assembly when the valve is blown open. Promptly upon release of air pressure, the check valve closes after each pumping stroke of the plunger 103. Air replenishment within the cylinder 114 under the piston 113, is provided for by means of a port 128 opening to atomsphere through the wall of the cylinder.

Air pressure created by the plunger 103, and more particularly the piston 113, and passing through the valve 121 is received in a chamber 129 below the base 115. The chamber 129 is provided by means of a cavity in a fitting 130 assembled with and complementary to and secured to the lower end of the barrel 101, as by means of an interlocking step joint 131. In the arrangement shown, the cylinder 114 is mounted on and between the barrel 101 and the fitting 130 by means of a lateral flange 132 extending from the base 115, and engaged on and hermetically sealed to a shoulder 133 facing upwardly on the fitting 130.

From the chamber 129, pressurized air is arranged to pass through a port 134 in a partition 135, dividing the chamber 129 from an air transfer subchamber 137. The subchamber 137 communicates with a passage 138 extending from the subchamber through the nipple 102 for delivering the pressurized air to a point of use such as an endotracheal tube cuff as described in connection with FIG. 1.

For monitoring the air pressure as it is generated by the pump plunger 103 in the chamber 129, as well as to monitor the prevailing pressure at the point of use with which the device 100 is connected by means of the nipple 102, a transparent sighting gauge tube 139 is mounted vertically at the front of the device within a vertical recess 40 between a crown overhang 141 at the forward end of crown of the barrel 101, and a corresponding foot projection 142, extending forwardly on the lower end portion of the fitting 130. At its lower, open end, the tube 139 is received in a socket 143 in the foot projection 142, and sealed by means of a ring seal 144. Communicating with the lower end of the tube 139 is a channel 145 in the fitting 130 communicating with a mercury reservoir 146, which opens upwardly into the pressure chamber 129. The reservoir 146 is normally filled with mercury to a height which, in the unpressurized condition of the device, locates the mercury level in the gauge tube bore at the lowest or zero gauge marking on the front of the tube 139. As shown, the tube 139 may have a graduated series of markings on and visible at the front of the device for checking the air pressure as reflected from the chamber 129 to the mercury. Mercury may be filled into the reservoir 146 through the outer end of the channel 145, which may then be sealed by means of a plug 147. Mercury impervious, but air pervious, means comprising a microporous membrane or screen 148 is secured fixedly across the top of the reservoir 146.

At its upper end, the gauge tube 139 is received in a downwardly opening socket 149 in the overhanging projection 141, and sealed by means of a ring seal 150. A relief space 151 in the upper end of the socket 149 provides a chamber for a float check valve 152, which may be in the form of a ball formed from N-buna rubber adapted to be thrust up into the dash-line position should there be a tendency for the mercury to overflow. The valve 152 thereby closes an air breather port 153, which is conveniently provided in a plug 154 closing the upper end of the bore providing the socket 149.

Although the mercury screen 148 may be reasonably depended upon to avoid mercury leakage into the pressure chamber 129, it may be noted that the port 134 is located at the top of the pressure chamber, so that the lower portion of the pressure chamber may serve as a safety sump. Should for any reason there still be a tendency for any leaked mercury to escape by way of the port 134 into the subchamber 137, further safety precaution against any mercury leakage into the passage 138 is provided by means of a collection sump 155 about the inner end of the passage 138. Since the passage 138 is separated from the port 134 by substantial space within the subchamber 137, an extremely high safety factor against mercury leakage is provided.

A digitally operable pressure relief plunger 157, is mounted in the barrel 101. At its upper end, the plunger 157 has an upwardly projecting button-like terminal 158, normally projecting above the lower portion of the slanted crown 105, and having its top end complementally slanted. The terminal 158, like the pump plunger terminal 104, is desireably non-circular, e.g. substantially rectangular in cross section as shown, to avoid turning, and is reciprocably loosely slidable in a complementary bore 159 in the crown portion of the barrel 101. At the lower end of the bore 159, a downwardly facing stop shoulder 160 is engagable by stop means 161, carried by the plunger 157, and which may be in the form of a transverse pin.

On its lower end portion within the barrel, the plunger 157 has an annular collar 162, providing a thrust shoulder for biasing means in the form of a coiled compression spring 163. This spring extends downwardly past the lower end portion of the plunger 157, and thrusts at its lower end against an annular shoulder 164 on the tubular body of a check valve 165. This shoulder 164 is seated on the upper end of a tubular upward extension 167 on the base 115 rearedly from the cylinder 114. The valve 165 is of the same commercially available general type as the valve 121. An elastomeric valve body 168 in the tubular housing of the valve 165 is normally biased to maintain a closed check valve engagement with a valve shoulder 169 until the pressure relief plunger 157 is depressed against the bias of the spring 163 to drive a depending plunger finger 170 downwardly against the upper end of the valve body 168. This unseats the valve body 168 from the valve seat 169, so that gas may escape upwardly through the valve assembly 165 from within the transfer subchamber 137.

In order to maintain close, accurate control over the relieving or exhausting of gas by means of the plunger 157, new and improved means are provided for restricting gas escape from the transfer chamber 137 to the exhaust system through the gas release passage controlled by the check valve 165. To this end, there is provided a complete closure at the bottom of the gas release passage stack provided by the tube 167, except for a port 171 about the lower end of which there is a depending annular collar 172 providing a socket within which is secured a flow restricting plug 173. The plug 173 controls the release or venting rate of gas from the gas transfer chamber 137 to the valve 165. In other words, regardless of the speed with which the plunger 157 is depressed to open the valve 165, the venting gas escape rate is controlled by the plug 173 to the degree of pressure drop desired.

The plug 173 may be made from a porous material which may comprise polyethylene, polypropylene, porous sintered metal, and the like, having a predetermined porosity. Plug porosity may range from 0.1 micron to 250 microns, depending on the venting rate desired. For the present purpose of tightly controlled venting in the use of the device 100, the plug 173 may be about 3/32 inch in thickness, and 3/16 inch in diameter and have a porosity of about 0.5 micron, and where the port 171 is of about 3/32 inch diameter. As a result, there is never a surge of vented gas, but always a slow, controlled, metered flow subject to virtually micrometer control to attain optimum pressure response in respect to the medical appliance with which the device 100 may be in use. It will be appreciated that although the porous plug and vent valve assembly has special value in respect to the pressure monitoring device 100, the venting valve and porous plug member 173 arrangement may have various other uses and that the size and porosity of the plug is readily adaptable to the size and degree of venting control desired through the venting valve.

In order to protect the nipple 102 against damage, as such, and to protect the coupling effected by means of the nipple 102, against antagonistic environmental objects, a substantial depending skirt 174 has been provided on the lower end of the fitting 130. This provides, in effect, a recessed cavity 175 in the bottom of the fitting 130 into which the nipple 102 extends freely for receiving a luer type connector.

The device 100 provides a substantially simplified arrangement, wherein the several components can be economically produced or obtained commercially. For example, the barrel 101 throughout most of its length comprises a one piece principal part. The fitting 130 comprises another one piece principal part which is neatly interfitted with and joined to the barrel. The cylinder 114, base 115, and the tube 167 are formed as another one piece single unit. The other elements of the assembly are all such as to interfit with one another or serve as moving parts in assembly with the three major body components of the device, and can be economically produced or commercially obtained and assembled.

It will be understood that variations and modifications may be effected without departing from the spirit and scope of the novel concepts of this invention.

I claim as my invention:

1. A hand held regulating and monitoring device, comprising:
    an elongate hollow barrel having a crown end sloping from a front side of the barrel toward a rear side of the barrel;
    a pressure monitoring gauge tube carried by said front side of said barrel and having gauging indicia thereon;
    a digitally operable air pressure generating plunger pump having a plunger head normally projecting above said crown end and the remainder of the plunger extending into said barrel and having pump mechanism within said barrel;
    a pressure chamber within said barrel and a check valve passage connecting said pump mechanism with said chamber;
    a mercury reservoir communicating with said chamber and with said gauge tube;
    air previous but mercury impervious means separating said reservoir from said chamber;
    a passage bypassing said reservoir and leading from said chamber and including means for connecting said bypass passage with a point of use of air pressure so that in the operation of said pump mechanism air pressure will be conducted to the point of use and to said reservoir;
    a check valved pressure release passage provided in said barrel in communication with said chamber; and
    means for opening said pressure release passage including a plunger reciprocable in a bore located in said barrel rearwardly from said plunger pump and having a digitally operable terminal projecting from said crown end a substantially shorter distance than the distance which said plunger heads projects from said crown end, so that said plunger head and said plunger terminal can be selectively operated by the same digit of a hand in which the device is held.

2. A device according to claim 1, including means for adjusting an initial mercury column height in said pressure gauge tube.

3. A device according to claim 2, wherein said adjusting means comprises a filler opening providing a supplement for said reservoir, and an adjustable plug in said opening.

4. A device according to claim 1, wherein said means for connecting said by-pass passage with a point of use comprises a fitting structure on the opposite end of said barrel from said crown end.

5. A generally fountain pen size hand held pressure regulating and monitoring device, comprising an elongate barrel having a crown end and an opposite end which includes means for attachment of the device to a point of gas pressure use; first depressable plunger means carried longitudinally within said barrel and having a terminal digitally engageable above said crown for operating this plunger means means for providing gas pressure in said barrel through check valve means; pressure monitoring means carried by said barrel; means for effecting communication of said gas pressure with said monitoring means and with said point of use; and second digitally depressible plunger means carried by said barrel in parallel relation to said first plunger means and having a digitally engageable terminal above said crown for selectively depressing said second plunger means for actuating a check valve for releasing said gas pressure from said means for effecting communication.

6. A device according to claim 5, wherein said first a passage extending throughout the length of said plunger, said plunger extending into said barrel and connected at its inner end to a collapsible resilient bellows with which the inner end of said passage connects, and said plunger and bellows providing an air pump connected through said check valved means in air pressure supplying relation with said communication effecting means.

7. A device according to claim 5, wherein said second digitally operable plunger means has its terminal projecting up from said crown end a substantially shorter distance than said first plunger means terminal projects above said crown end.

8. A device according to claim 5 wherein biasing means normally urge said plunger means towards said crown and for projection of said terminals thereabove, and stop shoulder means limiting the biased extension of said plunger means.

9. A device according to claim 5, wherein said first digitally operable plunger means comprises an actuator attached to a combination air pump and return spring bellows providing said means for providing gas pressure in said barrel.

10. A device according to claim 5, including a pressure release passage connected with said communication effecting means, and said valve means operated by said second plunger means comprising a check valve in said passage normally closing said passage against release of air from said communication effecting means, said release passage check valve being operable by an operating structure on said second plunger means for opening said passage to said communication effecting means when the second plunger means is depressed.

11. A device according to claim 5, wherein said communication effecting means includes an air pressure chamber, said pressure monitoring means comprises a pressure gauging tube mounted on the outside of said barrel parallel to said plunger means a reservoir for gauging fluid in communication with said chamber, and a passage connecting said reservoir and said gauging tube.

12. A device according to claim 11, including means for effecting a starting column adjustment of the gauging fluid in said gauging tube.

13. A device according to claim 12, wherein said communication effecting means includes a passage which bypasses said reservoir and connects said chamber with said point of use.

14. A device according to claim 5, wherein said crown slants from a front side of said barrel toward a rear side of said barrel, said first plunger means terminal projecting above said crown and forwardly spaced from a rear end portion of said crown, and said second plunger means terminal projecting above said rear end crown portion and to a lesser upward extent than said first plunger means terminal.

15. A device according to claim 5, wherein said barrel as originally constructed has its opposite end open, and all parts of the device which are received within the barrel being adapted to be assembled within the barrel from said open end, a fitting engaged with said opposite end and retaining said parts within the barrel, and said fitting including said means for attachment of the device to a point of gas pressure use.

16. A device according to claim 5, wherein said means for attachment to a point of gas pressure use comprises a nipple, and means providing a protective skirt about said nipple.

17. A device according to claim 5, wherein said check valve is located in an air release passage, and flow rate restricting means extending across said passage, said restricting means being in the form of a substantially uniformly porous member having dimensions selected for the size of said passage and a porosity for attaining pressure drop desired for the intended purpose.

18. A device according to claim 17, wherein said porous member comprises material selected from porous polyethylene, porous polypropolyene, and porous sintered metal.

19. A device according to claim 17, wherein said porous member has a porosity in a range from 0.01 microns to 250 microns.

20. A device according to claim 17, wherein said porous member comprises a material selected from porous polyethylene, porous polypropolyene, porous and porous sintered metal and has a porosity within a range of 0.01 microns to 250 microns.

21. A device according to claim 5, wherein said check valve is in an upwardly extending passage communicating at its lower end with said means for effecting communication, said second plunger means having a check valve actuating extension within said passage.

22. A device according to claim 5, including a vertical cylinder within said barrel, said first plunger means having a pump piston in said barrel, said check valve means being in the lower end of said barrel and communicating with said means for effecting communication, and means normally biasing said piston and first plunger upwardly from said valve means.

23. A generally fountain pen size hand held regulating and monitoring device comprising: an elongated hollow barrel having a crown end sloping from a front side of the barrel toward a rear side of the barrel; a pressure monitoring gauge tube carried by said front side of said barrel and having gauging indicia thereon; a digitally operable air pressure generating plunger pump having a plunger head normally projecting above said crown end and the remainder of the plunger extending into said barrel and having pump mechanism within said barrel; a pressure chamber within said barrel and a check valved passage connecting said pump mechanism with said chamber; passages leading from said chamber to said gauge tube and to means for connection with a point of use of air pressure so that in the operation of said pump mechanism air pressure will be conducted to the point of use and to said gauge tube; a check valved pressure release passage provided in said barrel in communication with said chamber; and means for opening said pressure release passage including a plunger reciprocable in a bore located in said barrel rearwardly from said plunger pump and on a lower portion of said sloping crown end and having a digitally operable terminal projecting from said crown end a substantially shorter distance than the distance which said plunger head projects from said crown end, so that said plunger head and said plunger terminal can be selectively operated by the same digit of a hand in which the device is held.

24. A device according to claim 23 wherein a fitting structure on the opposite end of said barrel from said crown end has said means for connecting a passage leading from said chamber with a point of use.

25. A device according to claim 24, wherein said fitting structure has a reservoir communicating with said chamber and with said gauge tube, and an air pervious but mercury impervious means separating said reservoir from said chamber.

26. A device according to claim 23, including a mercury reservoir commmunicating with said chamber and with said gauge tube, and an air pervious but mercury impervious means separating said reservoir from chamber.

27. A device according to claim 26, including means for adjusting an initial mercury column height in said pressure gauge tube.

28. A device acording to claim 27, wherein said adjusting means comprises a filler opening providing a supplement for said reservoir, and an adjusting plug in said opening.

29. A device according to claim 26, wherein one of said passages leads to said means for connection with a point of use and bypasses said mercury reservoir, and means defining a mercury collecting sump about an entrance into said one passage.

30. A device according to claim 26, including air relief means for said gauge tube, and means for permitting relief air passage through said air relief means, but for preventing escape of mercury.

31. A device according to claim 23, wherein said chamber has a partition dividing it into a pressurized air portion with which said pump mechanism communicates and a second portion divided from said first portion by a partition and communicating with said passage, said partition having an orifice effecting communication between said two portions of the chamber.

32. A generally fountain pen size hand held pressure regulating and monitoring device, comprising:
- an elongate barrel having a crown end and an opposite end which includes means for attachment of the device to a point of gas pressure use;
- first depressable plunger means carried longitudinally within said barrel and having a terminal digitally engageable above said crown for operating this plunger means for providing gas pressure in said barrel through check valve means;
- pressure monitoring means carried by said barrel;
- means for effecting communication of said gas pressure with said monitoring means and with said point of use;
- second digitally depressable plunger means carried by said barrel in parallel relation to said first plunger means and having a digitally engageable terminal above said crown for selectively depressing said second plunger means for actuating a check valve for releasing said gas pressure from said means for effecting communication;
- a passage having a port for receiving the released gas pressure into the passage from said means for effecting communication, and said second plunger means and said check valve being located in said passage; and
- means extending fixedly across said port for restricting flow of gas pressure through said port to a predetermined rate regardless of the speed with which said check valve may be opened by said second plunger means.

33. A device according to claim 32, wherein said restricting means is in the form of a substantially uniformly porous member having dimensions selected for a desired size and a porosity for attaining desired pressure drop across said member, said member being selected from porous polyethylene, porous polypropylene, and porous sintered metal.

34. A device according to claim 33, wherein said member has a porosity in a range of 0.01 micron to 250 microns.

35. A device according to claim 33, wherein said member is selected from porous polyethylene, polypropylene, and porous sintered metal, and has a porosity in a range of from 0.01 micron to 250 microns.

* * * * *